(12) United States Patent
Rasmussen

(10) Patent No.: US 10,281,373 B2
(45) Date of Patent: May 7, 2019

(54) SAMPLE INTRODUCTION SYSTEM

(71) Applicant: Siemens Healthcare Diagnostics Inc., Tarrytown, NY (US)

(72) Inventor: James E. Rasmussen, Plainville, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 131 days.

(21) Appl. No.: 15/643,024

(22) Filed: Jul. 6, 2017

(65) Prior Publication Data

US 2017/0299480 A1 Oct. 19, 2017

Related U.S. Application Data

(63) Continuation of application No. 14/398,259, filed as application No. PCT/US2013/039002 on May 1, 2013, now Pat. No. 9,726,582.

(60) Provisional application No. 61/642,820, filed on May 4, 2012.

(51) Int. Cl.
*G01N 1/28* (2006.01)
*B01L 3/00* (2006.01)

(52) U.S. Cl.
CPC .......... *G01N 1/28* (2013.01); *B01L 3/502715* (2013.01); *B01L 3/565* (2013.01); *B01L 2200/023* (2013.01); *B01L 2300/0816* (2013.01); *B01L 2300/123* (2013.01); *Y10T 436/2575* (2015.01)

(58) Field of Classification Search
CPC .. B01L 3/563; B01L 2200/026; F16L 21/005; F16L 19/0218; F16L 27/02
See application file for complete search history.

(56) References Cited

U.S. PATENT DOCUMENTS

| | | |
|---|---|---|
| 3,940,003 A | 2/1976 | Larson |
| 4,865,587 A | 9/1989 | Walling |
| 5,921,586 A | 7/1999 | Prassas et al. |
| 6,273,478 B1 | 8/2001 | Benett et al. |
| 6,425,424 B1 | 7/2002 | Ellis Calvo et al. |
| 6,960,198 B2 | 11/2005 | Sarmiento |
| 7,389,795 B2 | 6/2008 | Potter et al. |
| 2002/0173733 A1 | 11/2002 | Sarmiento |
| 2003/0195478 A1 | 10/2003 | Russo |
| 2005/0118068 A1 | 6/2005 | Kahl |
| 2009/0155838 A1 | 6/2009 | Hale |

(Continued)

FOREIGN PATENT DOCUMENTS

| | | |
|---|---|---|
| CN | 1507338 A | 6/2004 |
| CN | 1758961 A | 4/2006 |
| CN | 1846856 A | 10/2006 |

(Continued)

OTHER PUBLICATIONS

European Search Report and Written Opinion of European Application No. 13784110 dated Mar. 21, 2016.

(Continued)

*Primary Examiner* — Christopher Adam Hixson
(74) *Attorney, Agent, or Firm* — Kyle D. Petaja

(57) ABSTRACT

A sample port system/device associated with a fluid collection device is provided and is configured to receive fluid-containing devices of varying diameters. A method of improving the work flow and safety involved in acquiring and/or testing fluid samples using such sample port system/device is also provided.

23 Claims, 10 Drawing Sheets

(56) References Cited

U.S. PATENT DOCUMENTS

2010/0029014 A1    2/2010   Wang

FOREIGN PATENT DOCUMENTS

| | | |
|---|---|---|
| CN | 101010228 A | 8/2007 |
| CN | 101217994 A | 7/2008 |
| CN | 101754812 A | 6/2010 |
| CN | 101896276 A | 11/2010 |
| EP | 0351643 A2 | 1/1990 |
| EP | 1710016 A2 | 10/2006 |
| JP | S59131331 A | 7/1984 |
| JP | H03131274 A | 6/1991 |
| JP | H08304370 A | 11/1996 |
| JP | 2001337096 A | 12/2001 |
| JP | 2003530566 A | 10/2003 |
| JP | 2006518251 A | 8/2006 |
| JP | 2006292742 A | 10/2006 |
| WO | 0029111 A1 | 5/2000 |
| WO | 2004073864 A2 | 9/2004 |
| WO | 2007006306 A2 | 1/2007 |
| WO | 2007084183 A1 | 7/2007 |
| WO | 2008137008 A2 | 11/2008 |
| WO | 2011120024 A1 | 9/2011 |

OTHER PUBLICATIONS

International Search Report and Written Opinion of International Application No. PCT/US2013/039002 dated Sep. 16, 2013.

SAMPLE INTRODUCTION SYSTEM

CROSS-REFERENCE TO RELATED APPLICATIONS

This is a continuation application of U.S. Ser. No. 14/398,259, filed Oct. 31, 2014 which claims the benefit of U.S. National Stage of International Application No. PCT/US2013/039002, filed May 1, 2013 and claims priority under 35 U.S.C. 119(e) to U.S. Provisional Application Ser. No. 61/642,820, filed on May 4, 2012. All of the applications are incorporated by reference herein in their entirety.

STATEMENT REGARDING FEDERALLY SPONSORED RESEARCH OR DEVELOPMENT

None

1. FIELD OF THE INVENTION

The present invention relates in general to sample ports and microfluidic devices and systems and methods for using the same. More particularly, the present invention relates to a system and method for introducing a fluid sample to a medical diagnostic analyzer or microfluidic device.

2. BACKGROUND OF THE INVENTION

Fluid collection devices including, but not limited to, microfluidic devices and multi or single use medical diagnostic devices such as blood gas, hematology, and urinalysis testing devices/systems and the like, are useful in a variety of applications, including performance of chemical, clinical and environmental analyses of chemical or biological samples. Such devices are particularly well suited for analyses of minute quantities of samples, and can be produced at relatively low cost. Microfluidic devices typically include open ports for sample introduction, channels for transferring fluids, and can include chambers for storing reagents, pumps, valves, filters, etc.

The typical method of introducing a fluid sample to a microfluidic device has been to dispense the sample from the original collection device, like a syringe, onto the open port on the microfluidic device. In some case, like with the use of a vacutainer, it is sometimes necessary to first remove a portion of the fluid to be tested from the vacutainer by pipette or syringe, followed by dispensing the sample to the open port on the microfluidic device. Regardless of the exact method used, there exists a clear risk of a biohazard or chemical hazard spill when samples have to be dispensed to an open port. In addition, in cases like the use of a vacutainer described above, the use of multiple consumables is often required, which adds to the exposure risk and adds to the amount of chemical or biological hazardous waste which has to be handled and disposed. Also, dispensing samples manually to a fluid collection device not only presents a risk of exposure, but also ties up the hands of the technician, keeping them from other important tasks such as patient care, entering demographics, or other documentation tasks.

Thus, there is a clear need for an improved system or method or device useful in accomplishing the task of dispensing samples to a fluid collection device which minimizes risks of exposure and frees up time for the technician.

SUMMARY OF THE INVENTION

In accordance with an embodiment of the present invention, a port device or system for sample introduction to a fluid collection device is provided comprising:

a) a first section of a frusto-conical shape having a first end with an internal diameter A and a second end with an internal diameter B, wherein B is less than A;

b) a second section having a first end with an internal diameter C, a second end with an internal diameter D, a longitudinal axis extending from the first end to the second end, and a substantially circular internal surface along the longitudinal axis, wherein C is less than B, D is greater than C, and wherein the first end of the second section is in fluid flow communication with the second end of the first section;

c) a third section having a first end with an internal diameter E, a second end with an internal diameter F, a longitudinal axis extending from the first end to the second end, and a substantially circular internal surface along the longitudinal axis, wherein E is less than C, wherein F is greater than E, and wherein the first end of the third section is in fluid flow communication with the second end of the second section;

d) a base section having a first end with a diameter G and a second end, wherein G is less than E, wherein the first end of the base section is in fluid flow communication with the second end of the third section.

In accordance with an embodiment of the present invention, the first section of such port device or system is configured to accept and substantially seal the outer surface of a tip of a device having an outside diameter greater than B and less than A.

In accordance with an embodiment of the present invention, the second section of such port device or system is configured to accept and substantially seal the outer surface of a hollow tube having an outside diameter greater than or equal to C and less than D.

In accordance with an embodiment of the present invention, the third section of such port device or system is configured to accept and substantially seal the outer surface of a hollow tube having an outside diameter greater than or equal to E and less than C and less than F.

In accordance with an embodiment of the present invention, a port device or system for sample introduction to a fluid collection device is provided comprising a wall which is circular along its length, constructed of an elastomeric material, and comprising a first end having a first end internal diameter and a second end having a second end internal diameter; the wall having an inner surface defining at least a first sealing point having a first sealing point internal diameter and a second sealing point having a second sealing point internal diameter, each spaced between the first and second ends; wherein the second sealing point is located between the first sealing point and the second end; the wall further having an intermediate internal diameter at a location intermediate to the first and second sealing points; wherein the first sealing point internal diameter is less than the first end internal diameter and is less than the intermediate internal diameter; and wherein the second sealing point internal diameter is less than the intermediate internal diameter and less than the first sealing point internal diameter and is less than the second end internal diameter.

In accordance with an embodiment of the present invention, a process for dispensing a fluid is provided, utilizing such port device or system which is connected to a fluid collection device, and comprises inserting a fluid-containing device containing a fluid into the port device until substantially sealed; and transferring the fluid into the fluid collection device. The fluid collection device can be used in a medical setting, such as a point of care/near patient setting, a lab setting or the like. The fluid can be a liquid or a gas.

In accordance with an embodiment of the present invention, such port device or system is in fluid flow communication with an open inlet port of a fluid collection device.

DETAILED DESCRIPTION OF THE INVENTION

Figure 1A:
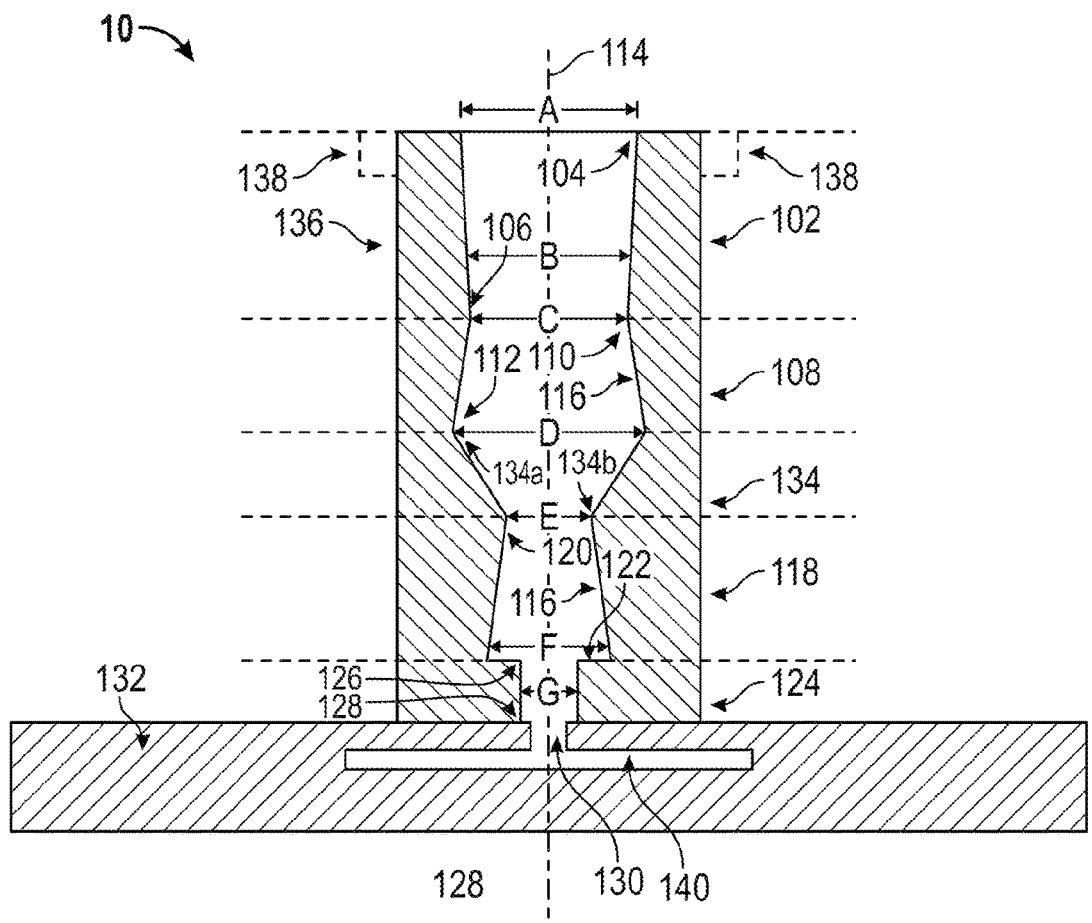
FIG. 1A is a cross-sectional view of a sample introduction port associated with a fluid collection device, which is shown by way of example as a microfluidic testing device.

Before explaining at least one embodiment of the invention in detail, it is to be understood that the invention is not limited in its application to the details of construction, the arrangement of the components, or the details or order of the process steps set forth in the following description or illustrated in the drawings. The invention is capable of other embodiments or of being practiced or carried out in various ways.

Also, it is to be understood that the phraseology and terminology employed herein is for purposes of description and should not be regarded as limiting.

The present invention relates to a sample introduction device/system, hereinafter referred to as a "port", which can accommodate a variety of sample introduction devices, such as, but not limited to, hollow tubes of various sizes, syringes, test tube luer adaptors, etc. The port is useful for transferring a fluid sample to a fluid collection device which can include, but is not limited to, a multi or single use medical diagnostic device such as blood gas, hematology, or urinalysis system or a microfluidic testing device, as either a part of such fluid collection device, or as connected to an open port in such fluid collection device. The fluid collection device can be selected from the group consisting of a multi or single use blood gas testing device or a microfluidic testing device. The port can be fixedly or detachably secured to the fluid collection device at an angle sufficient to allow for the transfer of fluid to the fluid collection device, and can be perpendicular to the surface of the fluid collection device. In the case of a microfluidic device, the port can also be secured to the top surface or a side surface of the fluid collection device. For example, the port can be (1) welded to the fluid collection device, such as by ultrasonic welding, (2) mechanically connected to the fluid collection device, such as by using one or more thread, (3) bonded to the fluid collection device using an adhesive or a cohesive, and (4) combinations thereof. The fluid sample can be any biological and/or medical fluid that can be tested and/or sampled with the aid of the fluid collection device. For example, the fluid sample can be selected from the group consisting of saliva, sputum, blood, urine, cerebral-spinal fluid, pleural fluid, dialysate and combinations thereof. In one embodiment, the port can be used to transfer both blood (e.g., for measuring HbA1C) and urine (e.g., for measuring Albumin/creatinine) to the fluid collection device.

The port can comprise, consist of, or consist essentially of at least one section or portion capable of receiving a fluid containing device, more preferably a first section, a second section, a third section, and a base section.

The first section is preferably of a frusto-conical shape and comprises, consists of, or consists essentially of a first end with an internal diameter A and a second end with an internal diameter B, wherein B is less than A. Internal diameter A can be at least about 2 and less than or equal to about 6 mm, more preferably at least about 3 and less than or equal to about 5 mm. Internal diameter B can be at least about 2 and less than about 6 mm, more preferably at least about 3 and less than or equal to about 5 mm.

The second section comprises, consists of, or consists essentially of a first end with an internal diameter C, a second end with an internal diameter D, a longitudinal axis extending from the first end to the second end, and a substantially circular internal surface along the longitudinal axis. Preferably, C is less than B, D is greater than C, and the first end of the second section is in fluid flow communication with the second end of the first section. Having internal diameter D greater than internal diameter C provides the benefits of: 1) giving the user a tactile feedback when seating a hollow tube into the port, and 2) preventing the hollow tube from being unintentionally squeezed back out of the port, which is more likely if D is not greater than C. Internal diameter C can be at least about 2 and less than about 6, preferably at least about 2 and less than or equal to about 5 mm. Internal diameter D can be at least about 2 and less than or equal to about 6 mm, preferably at least about 3 and less than or equal to about 5 mm.

The third section comprises, consists of, or consists essentially of a first end with an internal diameter E, a second end with an internal diameter F, a longitudinal axis extending from the first end to the second end, and a substantially circular internal surface along the longitudinal axis. Preferably, E is less than C, F is greater than E, and the first end of the third section is in fluid flow communication with the second end of the second section. Having internal diameter F greater than internal diameter E provides the benefits of: 1) giving the user a tactile feedback when seating a hollow tube into the port, and 2) preventing the hollow tube from being unintentionally squeezed back out of the port, which is more likely if F is not greater than E. Internal diameter E can be at least about 1 and less than or equal to about 4 mm, preferably at least about 1 and less than or equal to about 3.5 mm. Internal diameter F can be at least about 1 and less than or equal to about 4.5 mm, preferably at least about 1 and less than or equal to about 4 mm.

The base section comprises, consists of, or consists essentially of a first end with a diameter G and a second end. Preferably, G is less than E and the first end of the base section is in fluid flow communication with the second end of the third section. Internal diameter G can be at least about 0.1 and less than or equal to about 3 mm, preferably at least about 0.2 and less than or equal to about 1.5 mm.

The port can also further comprise a transition section disposed between the second section and the third section. The transition section can comprise, consist of, or consist essentially of a first end with an inside diameter of D and a second end with an inside diameter E. Preferably, the first end of the transition section is in fluid flow communication with the second end of the second section, and the second end of the transition section is in fluid flow communication with the first end of the third section.

At least one of the first, second, third, base, and optional transition sections of the port can be in fluid flow communication with other sections by connection of such section(s) to a neighboring section, such as by gluing, welding, fusion, etc. As an example, one or more of the sections, as a separate component, can be bonded or otherwise attached to another section or sections which is also a separate component. Also, at least one of the first, second, third, base, and optional transition sections of the port can be in fluid flow communication with another section by being a part of a solid unit along with such other neighboring section. As one example of such, the sections can all be a part of a single molded or formed port, or any two or more of the sections can each be a part of a single molded or formed component of the port.

The second end of the base section is in fluid flow communication with an open inlet port of a microfluidic testing device. Such fluid flow communication can be by connection of the second end of the base section with the open port, or the port and microfluidic testing device can be in fluid flow communication as components of a single molded or formed unit. Preferably, the connection of the second end of the base section to the open inlet port is a circumferentially sealed connection.

The port is preferably constructed of an elastomeric material, and more preferably is a thermoplastic elastomer such as a Kraton polymer material available from Kraton Polymers US LLC.

The port is preferably configured to accept a fluid sample and pass the fluid sample to the microfluidic testing device through the open inlet port. The first section is configured to accept and substantially seal the outer surface of a tip of a device having an outside diameter greater than B and less than A. Such device can be a syringe or test tube luer adaptor, and the tip is preferably substantially sealed at a location between the first and second ends of the first section.

The second section is configured to accept and substantially seal the outer surface of a hollow tube having an outside diameter greater than or equal to C and less than D. Preferably, the outer surface of the hollow tube is sealed at or near the first end of the second section. In addition, the first end of the third section, having a smaller diameter than such hollow tube, can serve as a stop for such hollow tube.

Similarly, the third section is configured to accept and substantially seal the outer surface of a hollow tube having an outside diameter greater than or equal to E and less than C and less than F. Preferably, the outer surface of the hollow tube is sealed at or near the first end of the third section. In addition, the first end of the base section, having a smaller diameter than such hollow tube, can serve as a stop for such hollow tube.

The first end of the first section can further comprise an outside surface having disposed thereon at least two tabs. Such tabs are preferably configured to receive at least one threaded portion of a syringe, thereby locking the syringe to the first end of the first section. The threaded portion of the syringe can be engaged by twisting it onto the tabs in order to lock the syringe in place.

The second and third sections can also be of a frusto-conical shape.

The port can also be a part of a microfluidic testing device comprising, consisting of, or consisting essentially of the sample port as described above, a first layer, a second layer disposed above the first layer and defining an open inlet port, and a component located between the first and second layers. The component(s) can include, but is not limited to, a pump, a chamber, a capillary, a reagent, an analyzer, and combinations thereof. The second end of the base section of the sample port is in fluid flow communication with the open inlet port defined by the second layer.

In addition, the present invention includes a process for dispensing a fluid comprising, consisting of, or consisting essentially of utilizing the microfluidic testing device described above, or another fluid collection device containing such sample port as described above; inserting a fluid-containing device containing a fluid into the sample port until substantially sealed; and transferring the fluid into the microfluidic testing device to a location between the first and second layers through the open inlet port. When the fluid-containing device is either a syringe or a test tube luer adaptor or some other such device having a tip with a diameter greater than B and less than A, then the outside surface of the tip is sealed within the first section upon insertion.

The fluid-containing device can also be a hollow tube having an outside diameter equal to or greater than C and less than D. Upon insertion, the outside surface of such hollow tube is sealed within the second section at a location at or near the first end of the second section.

The fluid-containing device can also be a hollow tube having an outside diameter equal to or greater than E and less than C and less than F. Upon insertion, the outside surface of such hollow tube is sealed within the third section at a location at or near the first end of the third section.

An embodiment of the present invention will now be described with reference to FIGS. 1A through 1E.

Referring now to FIG. 1A, therein is provided a cross-sectional view of a sample introduction port 10 connected to, or a part of, a microfluidic testing device 132.

A first section 102 of a frusto-conical shape has a first end 104 with an internal diameter A and a second end 106 with an internal diameter B, wherein B is less than A.

A second section 108 has a first end 110 with an internal diameter C, a second end 112 with an internal diameter D, a longitudinal axis 114 extending from the first end 110 to the second end 112, and a substantially circular internal surface 116 along the longitudinal axis 114, wherein C is less than B, D is greater than C, and wherein the first end 110 of the second section 108 is in fluid flow communication with the second end 106 of the first section 102.

A third section 118 has a first end 120 with an internal diameter E, a second end 122 with an internal diameter F, the same longitudinal axis 114 extending from the first end 120 to the second end 122, and substantially circular internal surface 116 along the longitudinal axis 114, wherein E is less than C, wherein F is greater than E, and wherein the first end 120 of the third section 118 is in fluid flow communication with the second end 112 of the second section 108.

A base section 124 has a first end 126 with a diameter G and a second end 128, wherein G is less than E, wherein the first end 126 of the base section 124 is in fluid flow communication with the second end 122 of the third section 118.

The second end 128 of the base section 124 is in fluid flow communication with an open inlet port 130 of microfluidic testing device 132. The port 10 can also include a transition section 134 disposed between the second section 108 and the third section 118 having a first end 134a with an inside diameter of D and a second end 134b with an inside diameter E, wherein the first end 134a of the transition section 134 is in fluid flow communication with the second end 112 of the second section 108, and wherein the second end 134b of the transition section 134 is in fluid flow communication with the first end 120 of the third section 118.

The first end 104 of the first section 102 can further include an outside surface 136 having disposed thereon at least two tabs 138. Further, microfluidic testing device 132 can also include a capillary or channel or chamber 140.

Figure 1B:
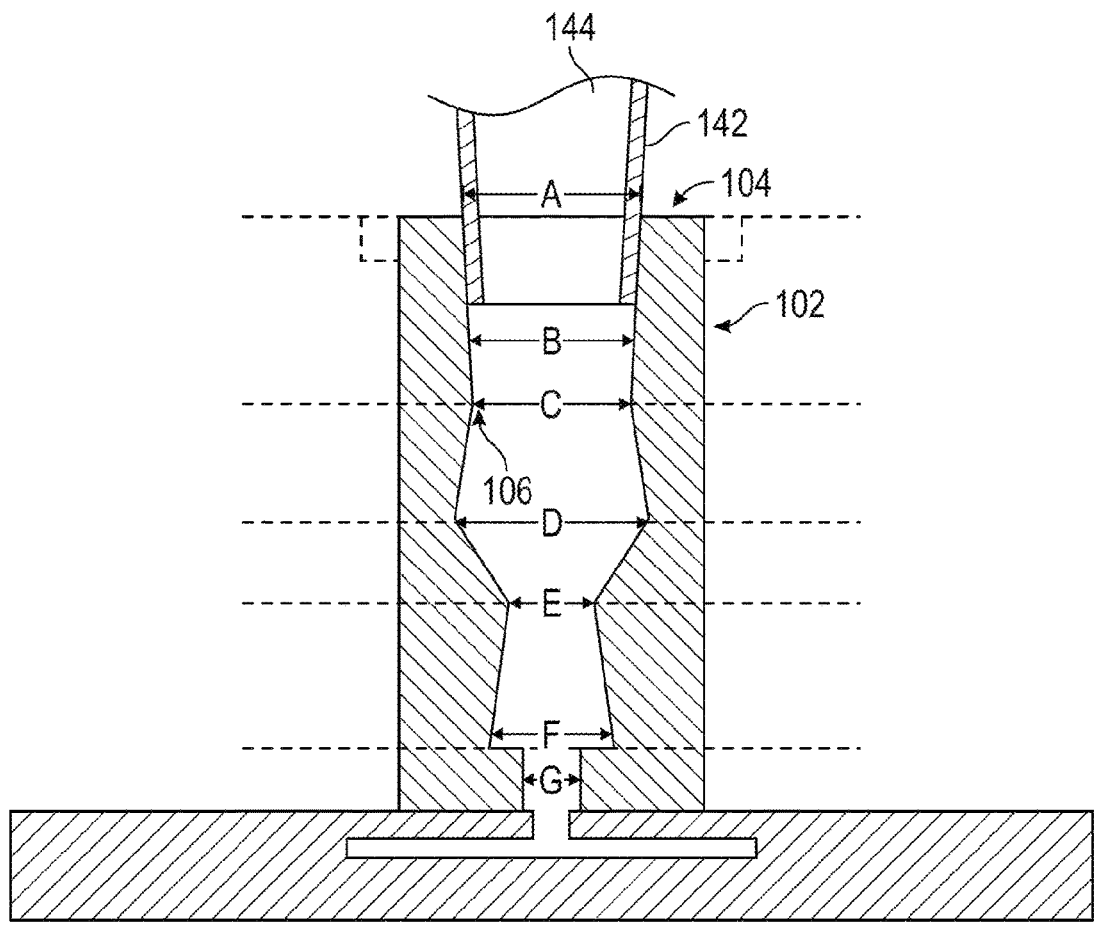
FIG. 1B is a cross-sectional view of a sample introduction port associated with a fluid collection device, which is shown by way of example as a microfluidic testing device also depicting the insertion of the tip of a device into the port.

Referring now to FIG. 1B, therein is provided a cross-sectional view of the sample introduction port connected to the microfluidic testing device from FIG. 1A, and also depicting the insertion of the tip of a device into the port.

The first section 102 is configured to accept and substantially seal the outer surface 142 of a tip of a device 144, wherein the tip of device 144 has an outside diameter greater than B and less than A. The tip of device 144 can be tapered as shown and is considered to be that portion which is capable of being accepted by first section 102.

Figure 1C:
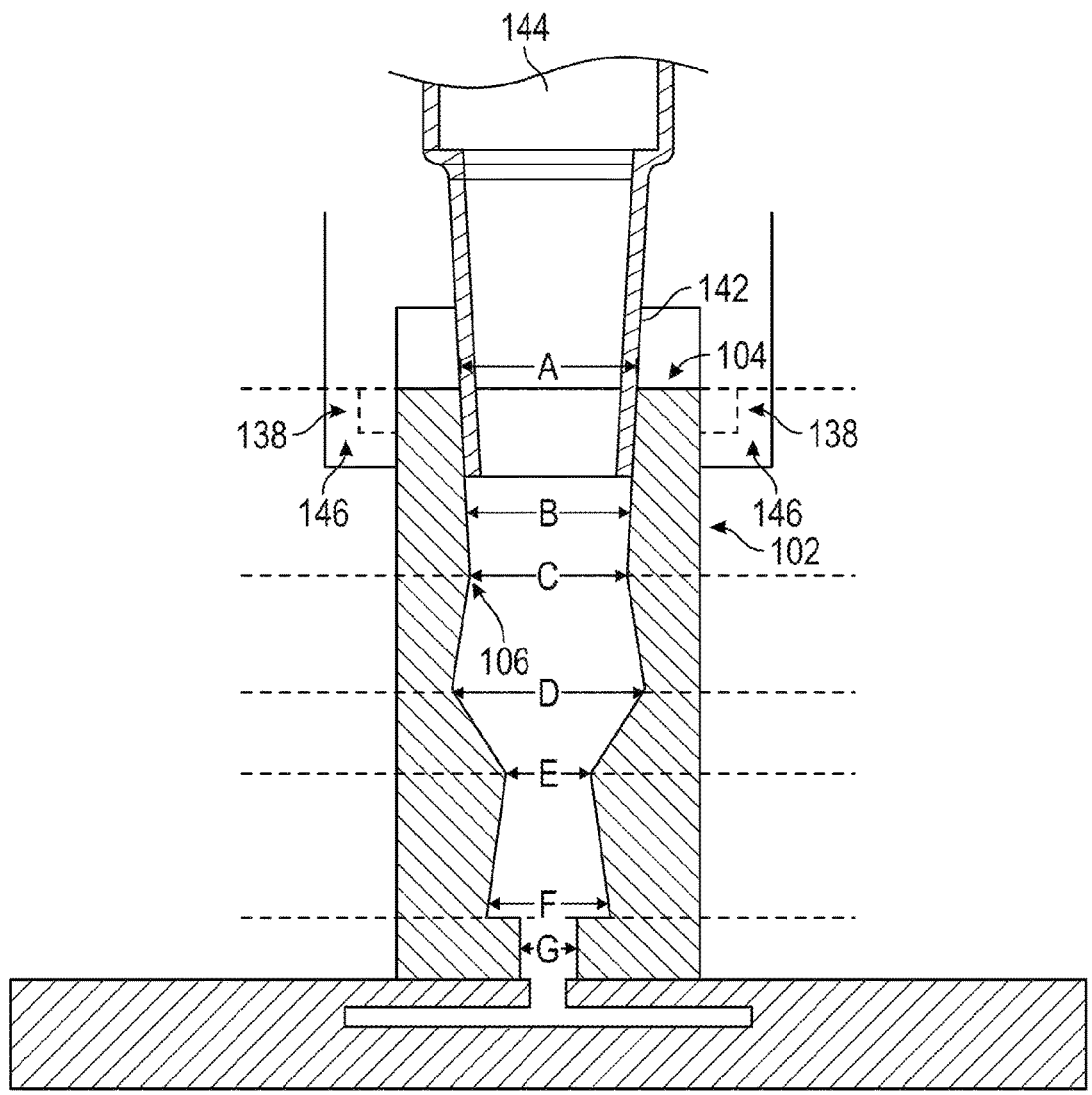
FIG. 1C is a cross-sectional view of a sample introduction port associated with a fluid collection device, which is shown by way of example as a microfluidic testing device also depicting the insertion of the tip of a syringe into the port with engagement of the syringe threads to tabs on the port.

Referring now to FIG. 1C, therein is provided a cross-sectional view of the sample introduction port 10 connected to the microfluidic testing device from FIG. 1A, and also depicting the insertion of the tip of a syringe 144 into the port 10 with engagement of the syringe threads 146 to tabs 138.

Figure 1D:
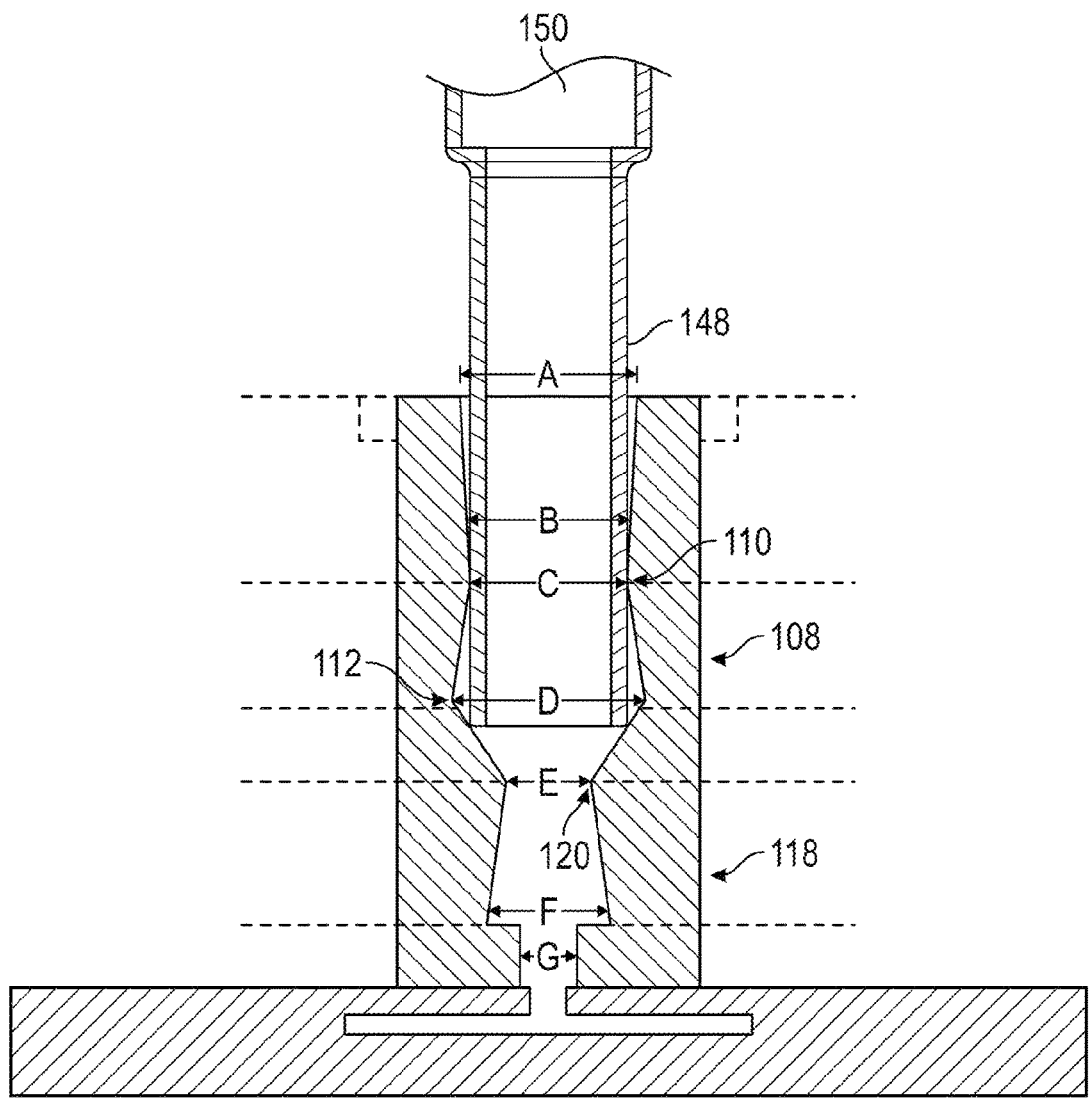
FIGS. 1D and 1E are each cross-sectional views of a sample introduction port associated with a fluid collection device, which is shown by way of example as a microfluidic testing device also depicting the insertion of a hollow tube into the port.

Referring now to FIG. 1D, therein is provided a cross-sectional view of the sample introduction port 10 connected to the microfluidic testing device from FIG. 1A also depicting the insertion of a hollow tube into the port 10.

The second section 108 is configured to accept and substantially seal an outer surface 148 of a hollow tube 150 having an outside diameter greater than or equal to C and less than D. The outer surface 148 of the hollow tube 150 is sealed at or near the first end 110 of the second section 108. The first end 120 of the third section 118 can serve as a stop for the hollow tube 150. Having internal diameter D greater than internal diameter C provides the benefits of: 1) giving the user a tactile feedback when seating hollow tube 150 into the port, and 2) preventing hollow tube 150 from being unintentionally squeezed back out of the port, which is more likely if D is not greater than C.

Figure 1E:
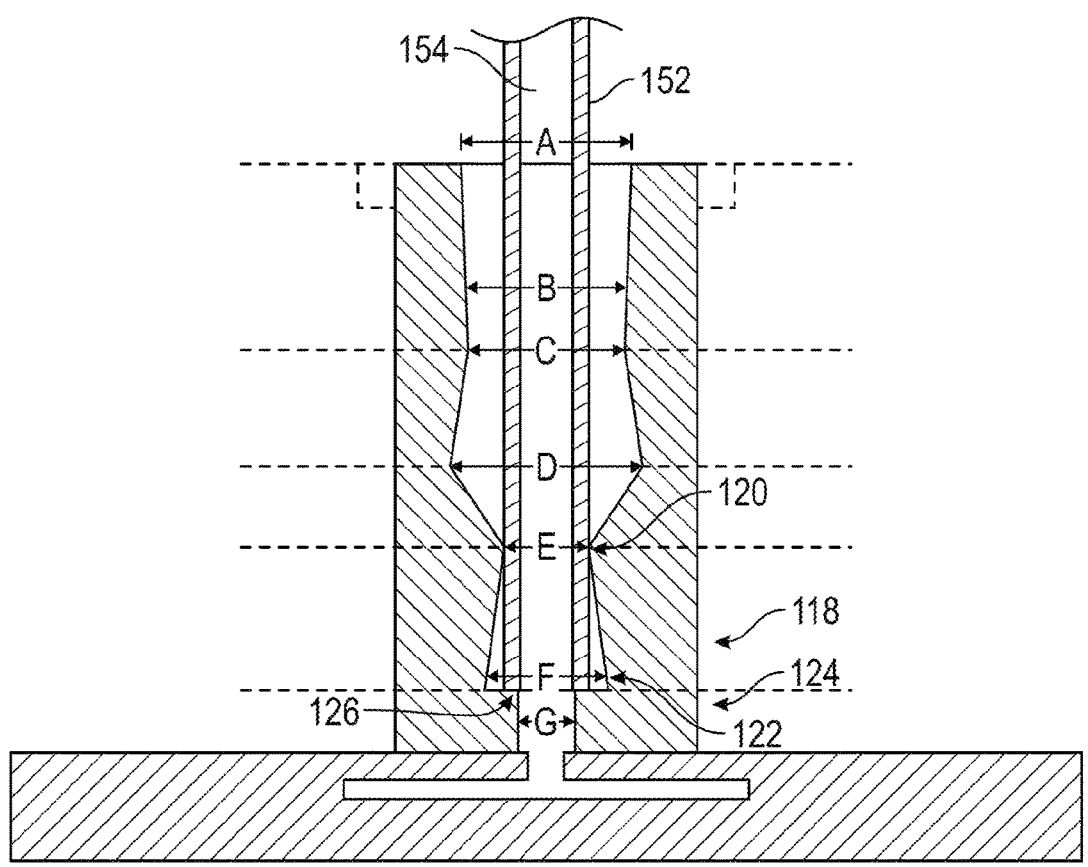

Referring now to FIG. 1E, therein is provided a cross-sectional view of the sample introduction port 10 connected to the microfluidic testing device from FIG. 1A also depicting the insertion of a hollow tube into the port 10.

The third section 118 is configured to accept and substantially seal an outer surface 152 of a hollow tube 154 having an outside diameter greater than or equal to E and less than C and less than F. The outer surface 152 of the hollow tube 154 is sealed at or near the first end 120 of the third section 118. The first end 126 of the base section 124 can serve as a stop for the hollow tube 154. Having internal diameter F greater than internal diameter E provides the benefits of: 1) giving the user a tactile feedback when seating hollow tube 154 into the port, and 2) preventing hollow tube 154 from being unintentionally squeezed back out of the port, which is more likely if F is not greater than E.

While not depicted in the Figures, it is to be understood that a hollow tube having an outside diameter which is less than or equal to G can be inserted into the base section 124. In addition, with reference to FIG. 1A, it is to be understood that a hollow tube having an outside diameter less than or equal to the outside diameter of the open inlet port 130 can be further inserted into open inlet port 130.

Figure 2:
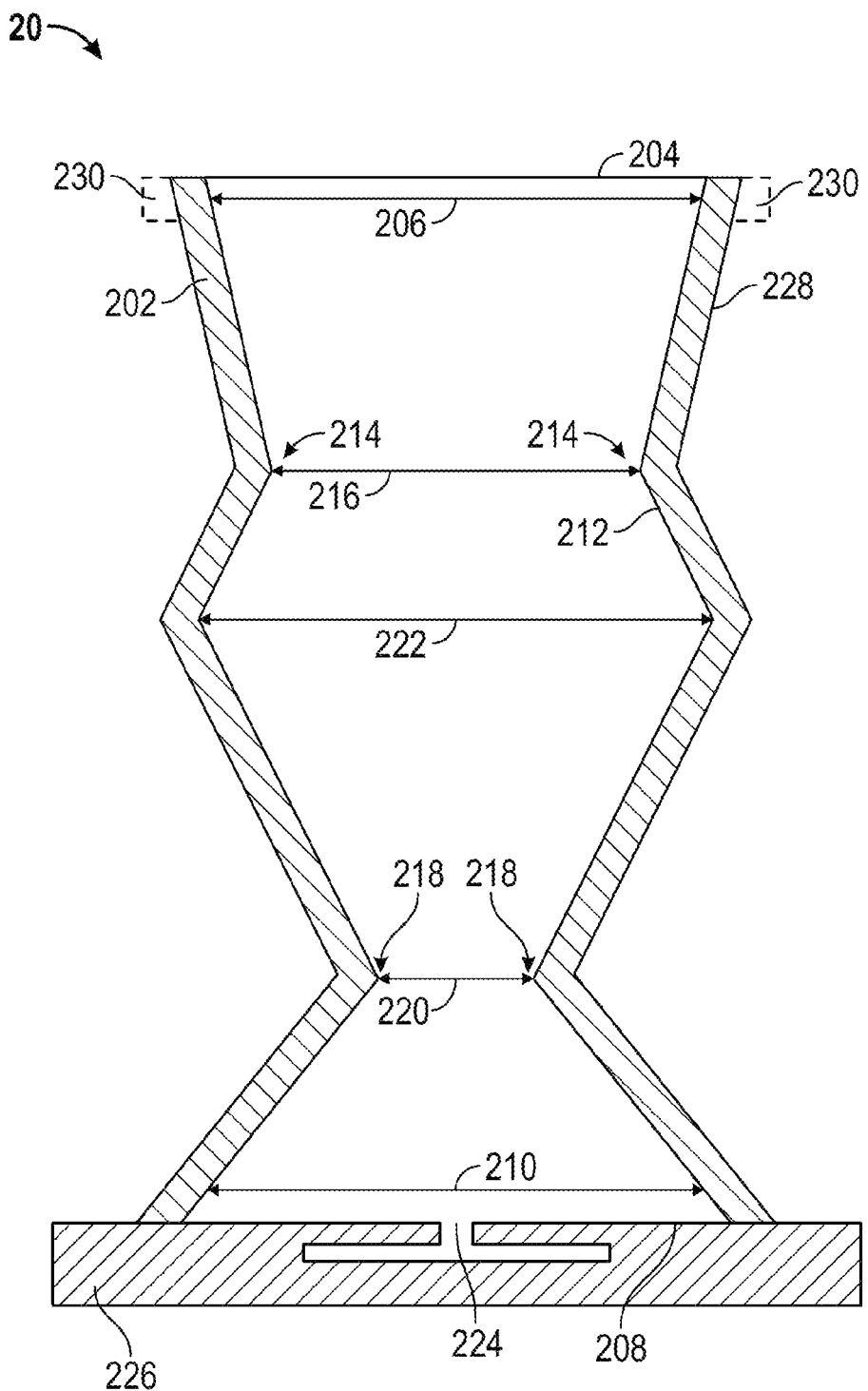
FIG. 2 is a cross-sectional view of a sample introduction port associated with a fluid collection device, which is shown by way of example as a microfluidic testing device.

Referring now to FIG. 2, therein is provided a cross-sectional view of a sample introduction port 20 representing another embodiment of the present invention.

A wall 202, which is circular along its length, has a first end 204 having a first end internal diameter 206 and a second end 208 having a second end internal diameter 210. The wall 202 can be constructed of an elastomeric material, preferably a thermoplastic elastomer. The wall 202 has an inner surface 212 defining at least a first sealing point 214 having a first sealing point internal diameter 216 and a second sealing point 218 having a second sealing point internal diameter 220. The first sealing point 214 and the second sealing point 218 are spaced between first end 204 and second end 208. Second sealing point 218 is also located between first sealing point 214 and second end 208. Wall 202 further has an intermediate internal diameter 222 at a location intermediate to the first sealing point 214 and the second sealing point 218. First sealing point internal diameter 216 is less than the first end internal diameter 206 and is less than the intermediate internal diameter 222. Second sealing point internal diameter 220 is less than the intermediate internal diameter 222 and less than the first sealing point internal diameter 216 and is less than the second end internal diameter 210.

The second end 208 of the port 20 can be in fluid flow communication with an open inlet port 224 of a microfluidic testing device 226. Such fluid flow communication can be by connecting second end 208 to open inlet port 224, as described above, preferably as a circumferentially sealed connection. The second end 208 and the microfluidic testing device 226 can also each be a part of a single molded or formed unit.

Port 20 is configured to accept a fluid sample and pass the fluid sample to the microfluidic testing device 226 through open inlet port 224.

The first end internal diameter 206 can be at least about 2 and less than or equal to about 6 mm, more preferably at least about 3 and less than or equal to about 5 mm. The second end internal diameter 210 can be at least about 1 and less than or equal to about 4.5 mm, more preferably at least about 1 and less than or equal to about 4 mm.

The first sealing point internal diameter 216 can be at least about 2 and less than about 6 mm, more preferably at least about 2 and less than or equal to about 5 mm.

The second sealing point internal diameter 220 can be at least about 1 and less than or equal to about 4 mm, more preferably at least about 1 and less than or equal to about 3.5 mm.

The intermediate internal diameter 222 can be at least about 2 and less than or equal to about 6 mm, more preferably at least about 3 and less than or equal to about 5 mm.

The port 20 is configured to accept and substantially seal the outer surface of a tip of a device wherein the tip of the device has an outside diameter greater than the first sealing point internal diameter 216 and less than the first end internal diameter 206. The tip of such device can be tapered as shown and is considered to be that portion which is capable of being accepted by port 20. Such device can be, but is not limited to, a syringe or test tube luer adaptor.

The port 20 is also configured to accept and substantially seal the outer surface of a hollow tube having an outside diameter greater than or equal to the first sealing point internal diameter 216 and less than the first end internal diameter 206. The outer surface of the hollow tube is preferably sealed at or near the first sealing point 214, and the second sealing point 218 can serve as a stop for the hollow tube. Having the first sealing point internal diameter 216 less than the intermediate internal diameter 222 provides the benefits of: 1) giving the user a tactile feedback when seating the hollow tube into the port 20, and 2) preventing the hollow tube from being unintentionally squeezed back out of the port 20, which is more likely if the first sealing point internal diameter 216 is not less than the intermediate internal diameter 222.

The port 20 is also configured to accept and substantially seal the outer surface of a hollow tube having an outside diameter greater than or equal to the second sealing point internal diameter 220 and less than the first sealing point internal diameter 216 and less than the second end internal diameter 210. The outer surface of such hollow tube is preferably sealed at or near the second sealing point 218. Having the second sealing point internal diameter 220 less than the second end internal diameter 210 provides the benefits of: 1) giving the user a tactile feedback when seating the hollow tube into the port 20, and 2) preventing the hollow tube from being unintentionally squeezed back out of the port 20, which is more likely if the second sealing point internal diameter 220 is not less than the second end internal diameter 210.

It is also to be understood that a hollow tube having an outside diameter which is less than or equal to the diameter of the open inlet port 224 can be inserted into the into open inlet port 224.

The first end 204 of the wall 202 can further comprise an outside surface 228 having disposed thereon at least two tabs 230. The tabs 230 are configured to receive at least one threaded portion of a syringe, thereby locking the syringe to the first end of the wall (similar to the description regarding FIG. 1C).

Figure 3A:
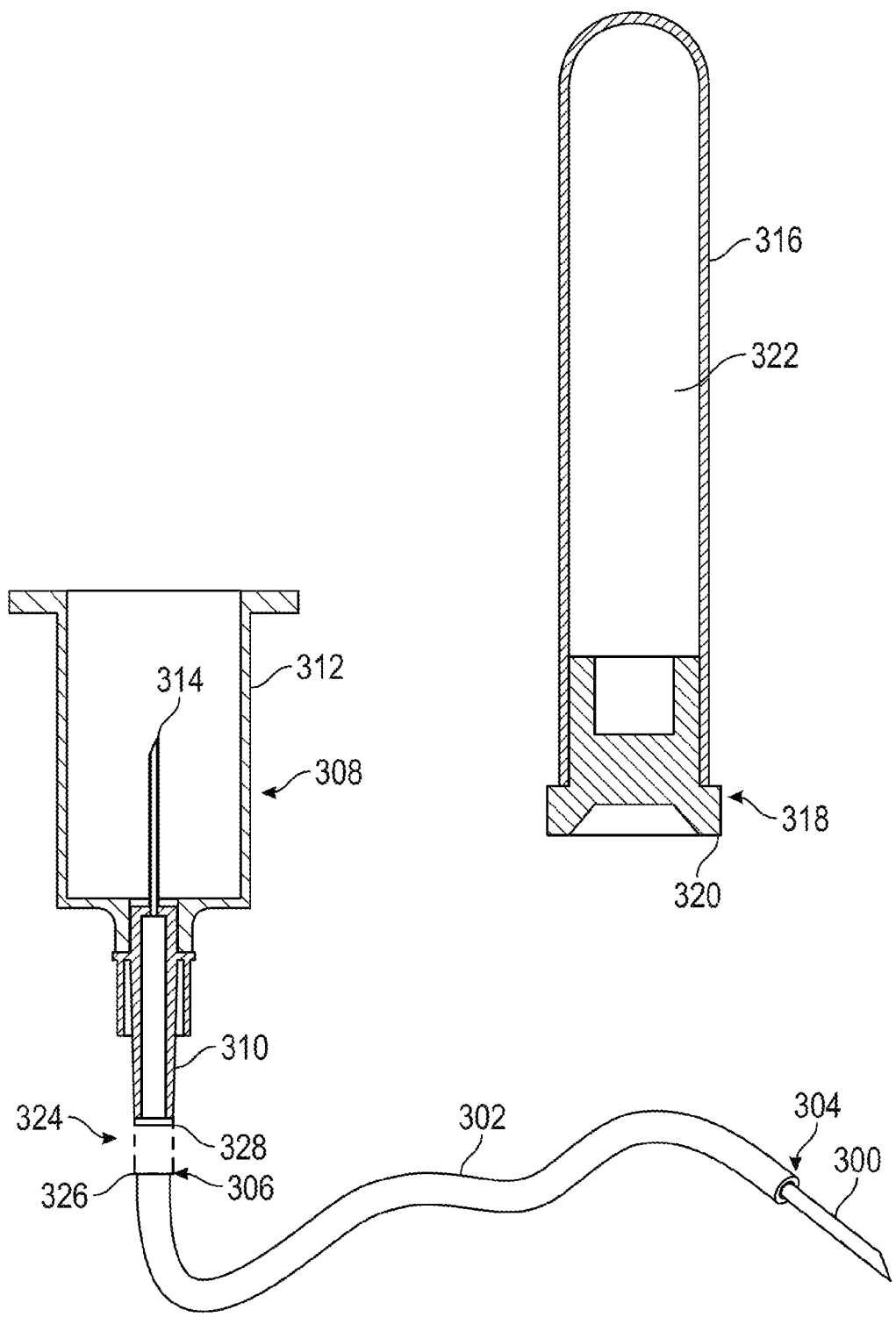
FIGS. 3A and 3B are schematic illustrations depicting a sample acquisition system and apparatus for acquiring a sample of blood from a vein.
Figure 3B:
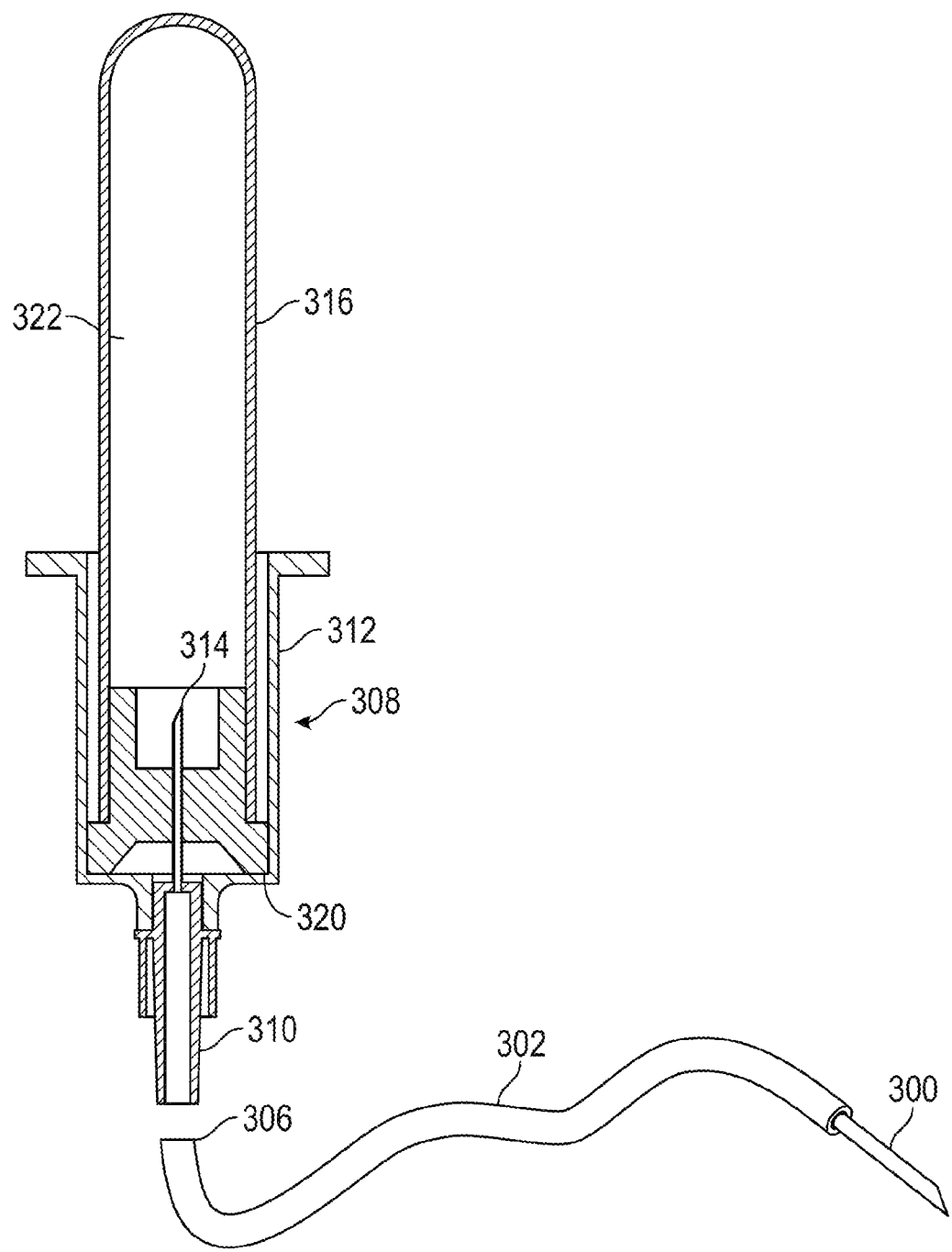
Figure 3C:
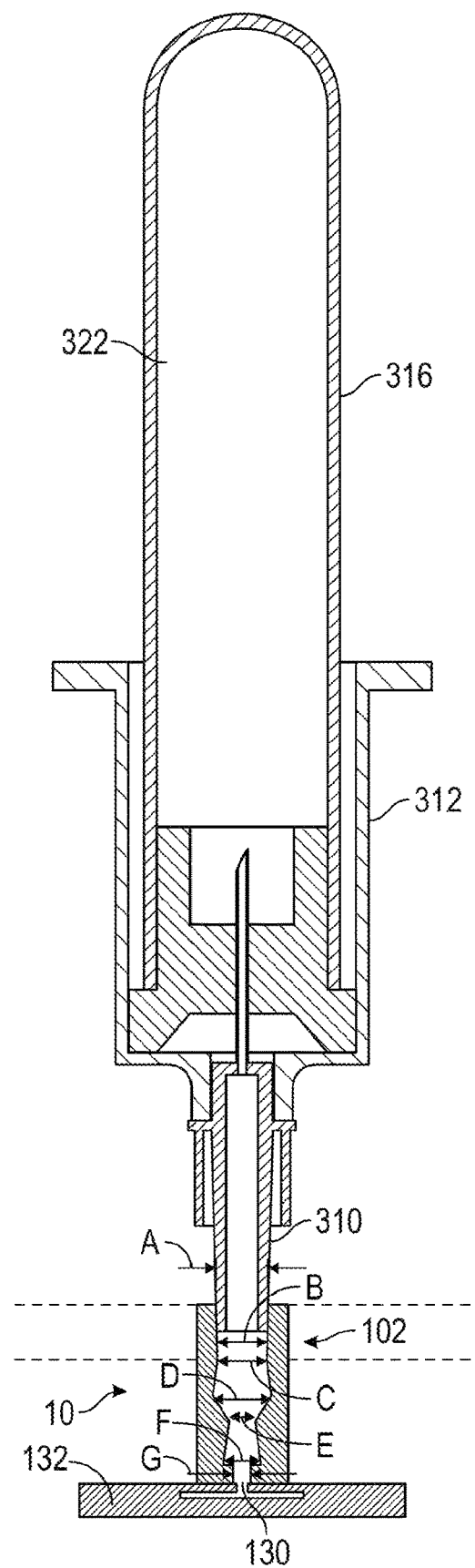
FIG. 3C is a schematic illustration depicting the insertion of the test tube/test tube luer adaptor from the sample acquisition system of FIGS. 3A and 3B into the sample introduction port of FIG. 1A.

Referring now to FIGS. 3A-3C, therein are depicted a method for collecting and delivering a blood sample to a microfluidic testing device.

Referring to FIG. 3A, therein is provided a schematic illustration depicting a sample acquisition system and apparatus for acquiring a sample of blood from a vein.

The method includes utilizing a sample acquisition system/assembly comprising, consisting of, or consisting essentially of: an intravenous needle 300; a tube 302 having a first end 304 and a second end 306; a test tube luer adaptor 308 comprising a male luer 310, which can be tapered as shown, and a female luer 312, wherein the female luer 312 comprises a hollow needle 314 in fluid flow communication with the male luer 310; a test tube 316 having an open end 318 sealed with an elastomeric sealing member 320, wherein the test tube 316 and the elastomeric sealing member 320 define a space 322 having a pressure lower than atmospheric pressure, preferably less than 1 atmosphere.

The intravenous needle 300 is connected in fluid flow communication with the first end 304 of the tube 302, and the second end 306 of the tube 302 is connected in fluid flow communication with the male luer 310 of the test tube luer adaptor 308. The system can also comprise a connector 324 having a first end 326 and a second end 328, wherein the first end 326 of connector 324 is connected in fluid flow communication to the second end 306 of tube 302 and wherein the second end 328 of connector 324 is connected in fluid flow communication to the male luer 310, thereby establishing a fluid flow communication between the second end 306 of tube 302 and male luer 310.

Intravenous needle 300 is inserted into a vein containing blood, establishing a pathway for blood to flow from the vein to the test tube luer adaptor 308.

Referring now to FIG. 3B, test tube 316 is inserted into the female luer 312 of the test tube luer adaptor 308 such that the hollow needle 314 punctures through the elastomeric sealing member 320, thereby drawing blood from the vein into space 322 of test tube 316. The second end 306 of tube 302 (or the second end 328 of connector 324, if used) is removed from the male luer 310.

Figure 3D:
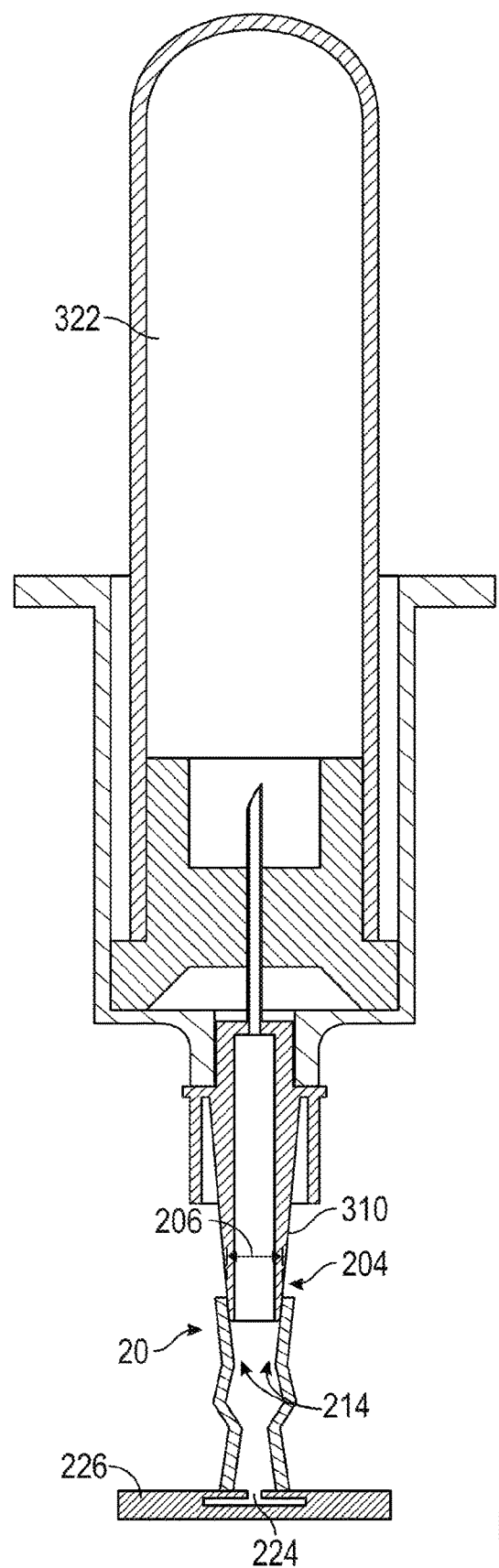
FIG. 3D is a schematic illustration depicting the insertion of the test tube/test tube luer adaptor from the sample acquisition system of FIGS. 3A and 3B into the sample introduction port of FIG. 2.

Referring now to FIGS. 3C and 3D, the male luer 310 is then inserted into the sample introduction port described above.

As shown in FIG. 3C, the male luer 310 is inserted into the first section 102 of sample port 10 until substantially sealed within the first section 102. Blood is then transferred from space 322 into the microfluidic testing device 132 through the open inlet port 130.

As shown in FIG. 3D, the male luer 310 is inserted into port 20 through first end 204 until substantially sealed at a location between first end 204 and first sealing point 214. Blood is then transferred from space 322 into the microfluidic testing device 226 through open inlet port 224.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

Further, unless expressly stated otherwise, the term "about" as used herein is intended to include and take into account variations due to manufacturing tolerances and/or variabilities in process control.

Changes may be made in the construction and the operation of the various components, elements and assemblies described herein, and changes may be made in the steps or sequence of steps of the methods described herein without departing from the spirit and the scope of the invention as defined in the following claims.

What is claimed is:

1. A port comprising:
   a) a first section having a frusto-conical shape, a first end with an internal diameter A, and a second end with an internal diameter B, wherein B is less than A;
   b) a second section having a frusto-conical shape, a first end with an internal diameter C, a second end with an internal diameter D, a longitudinal axis extending from said first end to said second end, and a substantially circular internal surface along said longitudinal axis, wherein C is less than B, D is greater than C, and wherein said first end of said second section is adjacent to and in fluid flow communication with said second end of said first section;
   c) a transition section having a frusto-conical shape, a first end with an inside diameter of D and a second end with an inside diameter E, wherein D is greater than E, wherein said first end of said transition section is adjacent to and in fluid flow communication with said second end of said second section;

d) a third section having a frusto-conical shape, a first end with an internal diameter E, a second end with an internal diameter F, a longitudinal axis extending from said first end to said second end, and a substantially circular internal surface along said longitudinal axis, wherein E is less than C, wherein F is greater than E, and wherein said first end of said third section is adjacent to and in fluid flow communication with said second end of said transition section;

e) a base section having a first end with a diameter G and a second end, wherein G is less than E, wherein said first end of said base section is adjacent to and in fluid flow communication with said second end of said third section.

2. The port of claim 1 wherein said second end of said base section is in fluid flow communication with an open inlet port of a fluid collection device selected from the group consisting of a microfluidic testing device and a multi or single use testing device.

3. The port of claim 2 wherein said second end of said base section is either fixedly or detachably connected in fluid flow communication with said open inlet port.

4. The port of claim 3 wherein the connection of said second end of said base section to said open inlet port is a circumferentially sealed connection.

5. The port of claim 2 configured to accept a fluid sample and pass said fluid sample to said microfluidic testing device through said open inlet port.

6. The port of claim 1 wherein said port is constructed of an elastomeric material.

7. The port of claim 1 wherein said first section is configured to accept and substantially seal the outer surface of a tip of a device having an outside diameter greater than B and less than A.

8. The port of claim 7 wherein said device is a syringe or test tube luer adaptor.

9. The port of claim 7 wherein said tip is substantially sealed at a location between said first and second ends of said first section.

10. The port of claim 1 wherein said second section is configured to accept and substantially seal the outer surface of a hollow tube having an outside diameter greater than or equal to C and less than D.

11. The port of claim 10 wherein said outer surface of said hollow tube is sealed at or near said first end of said second section.

12. The port of claim 11 wherein said transition section serves as a stop for said hollow tube.

13. The port of claim 1 wherein said transition section is configured to accept and substantially seal the outer surface of a hollow tube having an outside diameter greater than or equal to E and less than C.

14. The port of claim 13 wherein said outer surface of said hollow tube is sealed by the transition section.

15. The port of claim 14 wherein said first end of said base section serves as a stop for said hollow tube.

16. The port of claim 1 wherein said first end of said first section further comprises an outside surface having disposed thereon at least two tabs.

17. The port of claim 16 wherein said tabs are configured to receive at least one threaded portion of a syringe, thereby locking said syringe to said first end of said first section.

18. A microfluidic testing device comprising:
a) a first layer;
b) a second layer disposed above said first layer and defining an open inlet port;
c) a component located between said first and second layers, wherein said component is selected from the group consisting of a pump, a chamber, a capillary, a reagent, an analyzer, and combinations thereof;
d) a sample port comprising:
   i) a first section having a frusto-conical shape having a first end with an internal diameter A and a second end with an internal diameter B, wherein B is less than A;
   ii) a second section having a frusto-conical shape, a first end with an internal diameter C, a second end with an internal diameter D, a longitudinal axis extending from said first end to said second end, and a substantially circular internal surface along said longitudinal axis, wherein C is less than B, D is greater than C, and wherein said first end of said second section is adjacent to and in fluid flow communication with said second end of said first section;
   iii) a transition section having a frusto-conical shape, a first end with an inside diameter of D and a second end with an inside diameter E, wherein D is greater than E, wherein said first end of said transition section is adjacent to and in fluid flow communication with said second end of said second section;
   iv) a third section having a frusto-conical shape, a first end with an internal diameter E, a second end with an internal diameter F, a longitudinal axis extending from said first end to said second end, and a substantially circular internal surface along said longitudinal axis, wherein E is less than C, wherein F is greater than E, and wherein said first end of said third section is adjacent to and in fluid flow communication with said second end of said transition section;
   v) a base section having a first end with a diameter G and a second end, wherein G is less than E, wherein said first end of said base section is adjacent to and in fluid flow communication with said second end of said third section; and
e) wherein said second end of said base section of said sample port is in fluid flow communication with said open inlet port.

19. A process for dispensing a fluid comprising:
a) utilizing the microfluidic testing device of claim 18;
b) inserting a fluid-containing device containing a fluid into said sample port until substantially sealed; and
c) transferring said fluid into said microfluidic testing device, between said first and second layers, through said open inlet port.

20. The process of claim 19 wherein said fluid-containing device is either a syringe or a test tube luer adaptor having a tip with a diameter greater than B and less than A, and wherein the outside surface of said tip is sealed within said first section upon insertion per step b).

21. The process of claim 20 wherein said fluid-containing device is a syringe, wherein said first end of said first section further comprises an outside surface having disposed thereon at least two tabs configured to receive at least one threaded portion of a syringe, and wherein said threaded portion of said syringe is engaged by twisting onto said tabs in order to lock said syringe to said first end of said first section.

22. The process of claim 19 wherein said fluid-containing device is a hollow tube having an outside diameter equal to or greater than C and less than D, and wherein the outside surface of said hollow tube is sealed, upon insertion per step b), within said second section at or near said first end of said second section.

23. The process of claim 19 wherein said fluid-containing device is a hollow tube having an outside diameter equal to or greater than E and less than C and less than F, and wherein the outside surface of said hollow tube is sealed, upon insertion per step b), within said transition section.

* * * * *